United States Patent
Waxman et al.

(10) Patent No.: US 7,641,638 B2
(45) Date of Patent: Jan. 5, 2010

(54) FLEXIBLE ELONGATE SURGICAL NEEDLE DEVICE HAVING A TISSUE ENGAGING SECTION BEING OF GREATER FLEXIBILITY THAN AN INTERMEDIATE SECTION, AND METHODS OF USING THE DEVICE

(75) Inventors: Irving Waxman, Chicago, IL (US); David F. Waller, Winston-Salem, NC (US)

(73) Assignee: Wilson-Cook Medical Inc., Winston Salem, NC (US)

( * ) Notice: Subject to any disclaimer, the term of this patent is extended or adjusted under 35 U.S.C. 154(b) by 482 days.

(21) Appl. No.: 11/304,218

(22) Filed: Dec. 14, 2005

(65) Prior Publication Data

US 2006/0189891 A1 Aug. 24, 2006

Related U.S. Application Data

(60) Provisional application No. 60/636,175, filed on Dec. 15, 2004.

(51) Int. Cl.
*A61M 5/00* (2006.01)
*A61M 5/32* (2006.01)
(52) U.S. Cl. .................................. 604/264; 604/272
(58) Field of Classification Search ............ 604/173.01, 604/533, 264, 272, 273, 523–525; 600/564
See application file for complete search history.

(56) References Cited

U.S. PATENT DOCUMENTS

| | | | |
|---|---|---|---|
| 6,419,641 B1 | 7/2002 | Mark et al. | |
| 6,425,887 B1 * | 7/2002 | McGuckin et al. | 604/272 |
| 6,855,124 B1 * | 2/2005 | Gonzalez et al. | 604/96.01 |
| 7,048,694 B2 | 5/2006 | Mark et al. | |
| 7,435,240 B2 * | 10/2008 | Barkhahn et al. | 604/272 |
| 2002/0013539 A1 | 1/2002 | Hung | |
| 2003/0187382 A1 * | 10/2003 | Unsworth | 604/19 |
| 2003/0208136 A1 | 11/2003 | Mark et al. | |
| 2004/0133124 A1 * | 7/2004 | Bates et al. | 600/564 |
| 2004/0199050 A1 * | 10/2004 | Richardson | 600/116 |

OTHER PUBLICATIONS

Search Report and Written Opinion dated Mar. 29, 2006, for International Application No. PCT/US2005/045264.
Echo Tip® Ultrasound Needle, Cook®, Wilson-Cook Medical GI Endoscopy, Winston-Salem, North Carolina (prior to Dec. 15, 2004).
International Preliminary Report on Patentability dated Apr. 5, 2007 for International Application No. PCT/US2005/045264 filed on Dec. 14, 2005.

* cited by examiner

*Primary Examiner*—Kevin C Sirmons
*Assistant Examiner*—Andrew M Gilbert
(74) *Attorney, Agent, or Firm*—Brinks Hofer Gilson & Lione

(57) ABSTRACT

Medical devices, kits, and methods for utilizing an elongate surgical needle that may be used through an endoscope working channel or through an external accessory channel device used with an endoscope are provided. The needle has a proximal end and a flexible distal end, an opening at or near the proximal end and an opening at or near the distal end, the openings defining a channel. The surgical needle distal end comprises a tissue engaging section and an intermediate section being operatively coupled in an axial direction. The tissue engaging section and intermediate section have different flexibility such that the tissue engaging section has greater flexibility than the intermediate section. Optionally, the needle distal end has a preformed bend at or near the tissue engaging section, the preformed bend capable of being constrained to a substantially linear configuration and capable of returning to the preformed configuration when unconstrained.

20 Claims, 7 Drawing Sheets

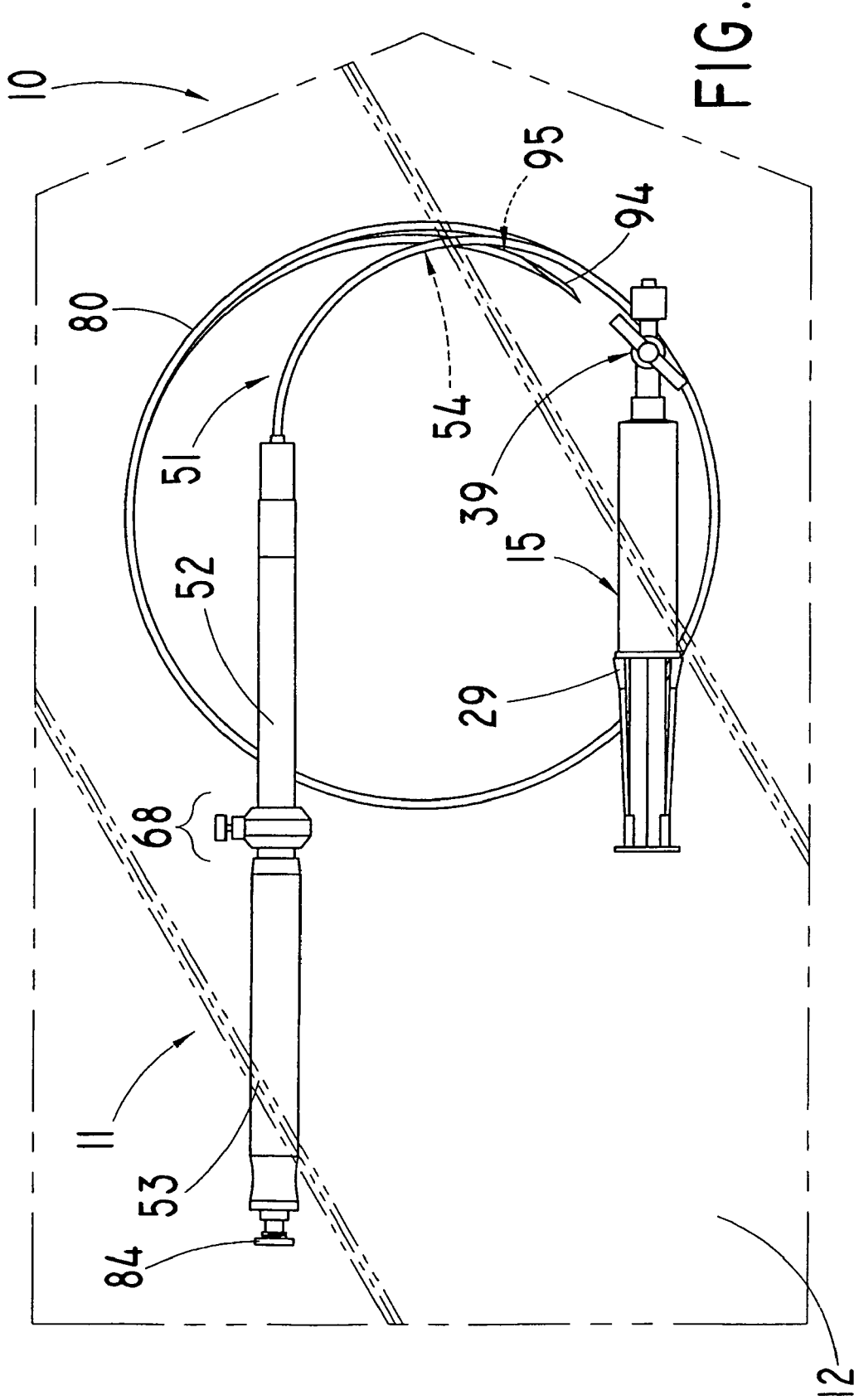

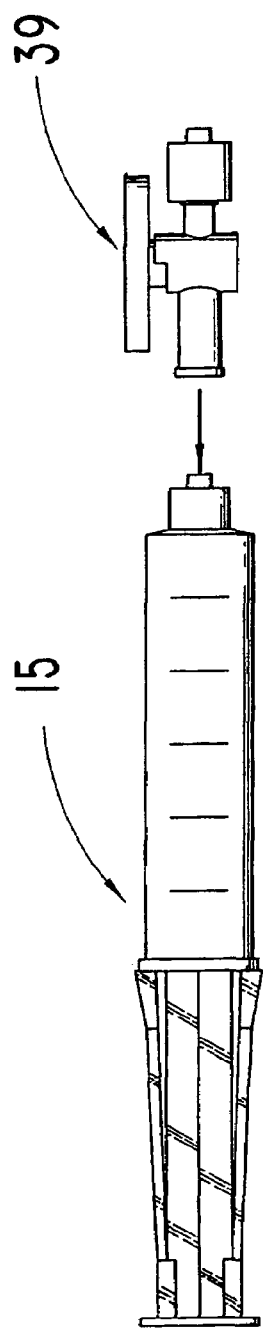
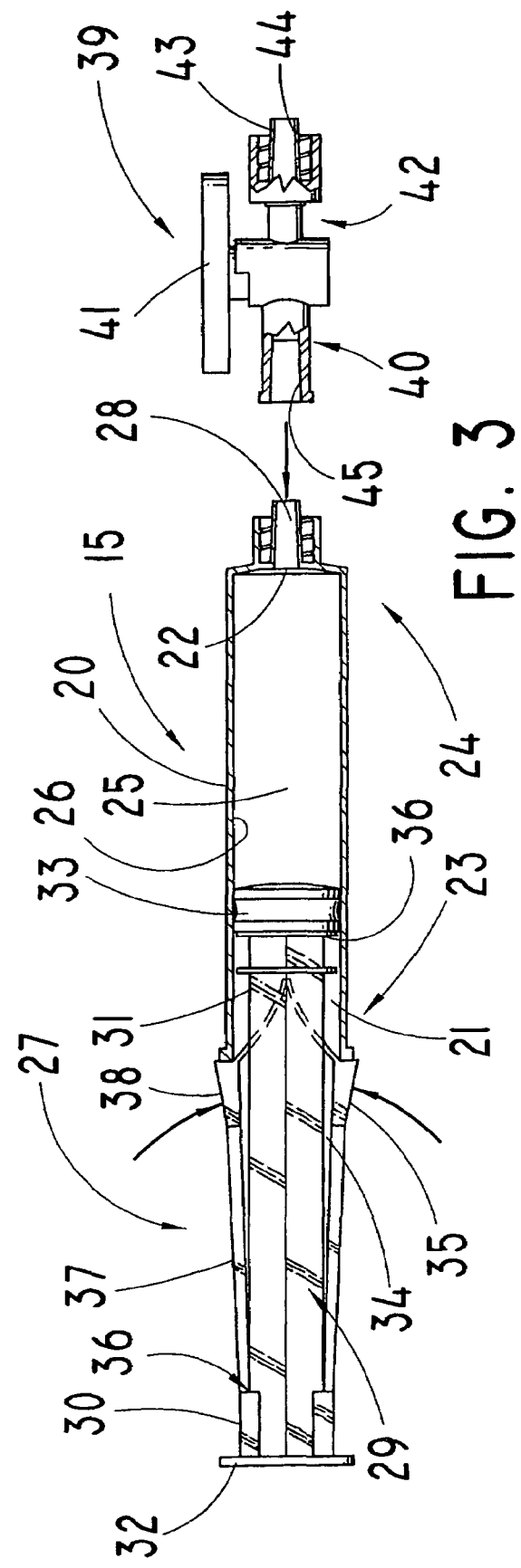

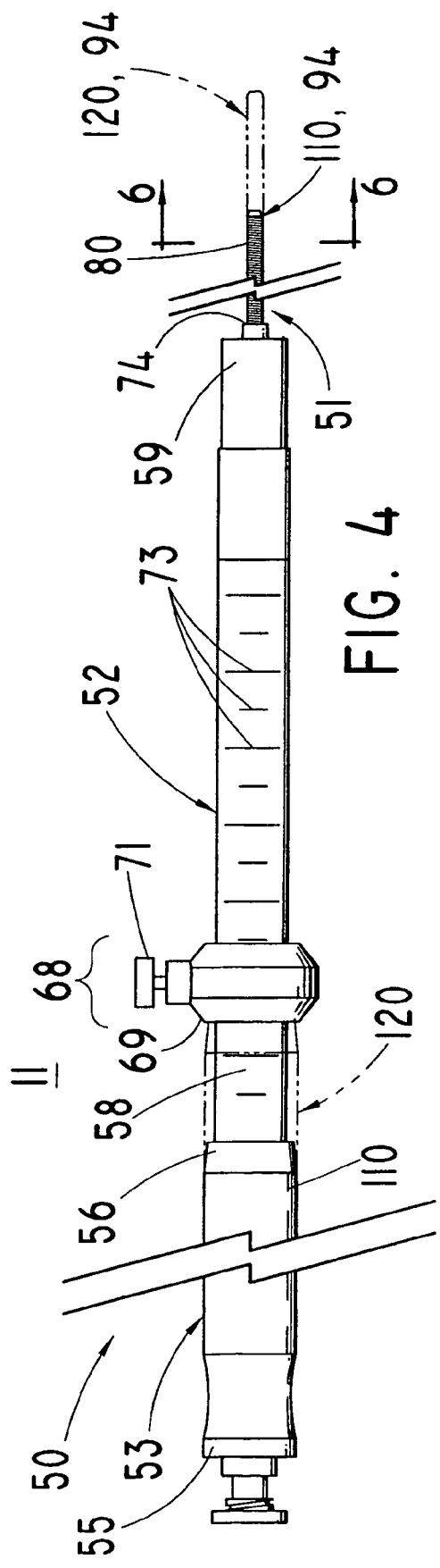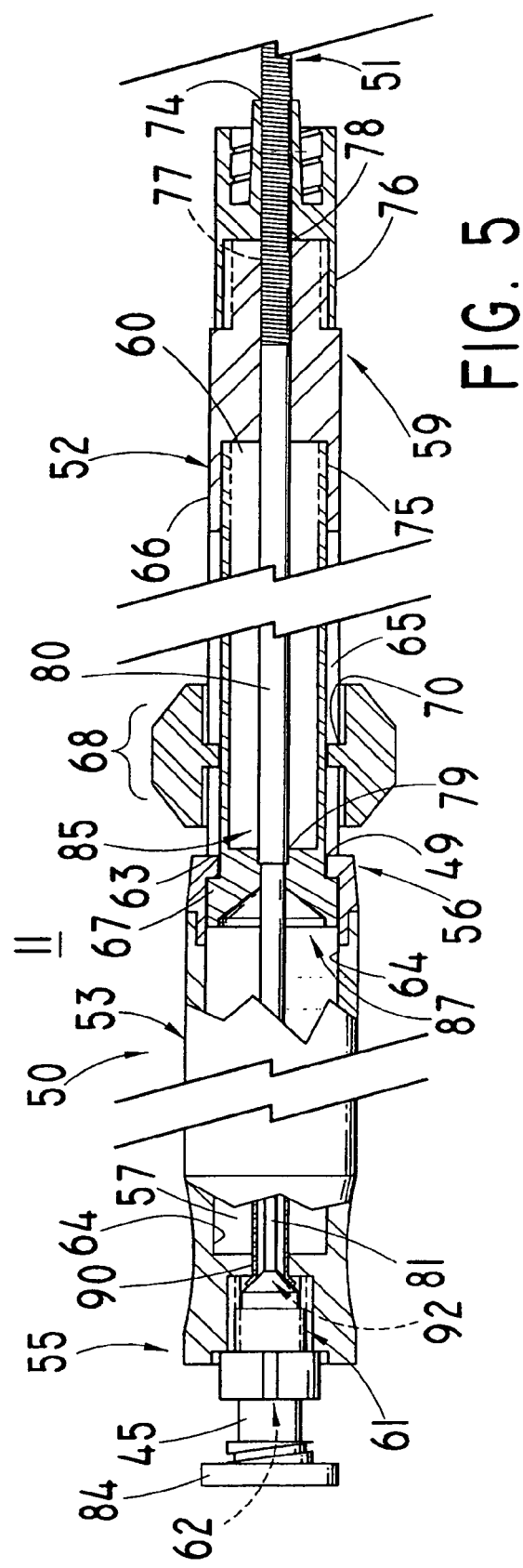

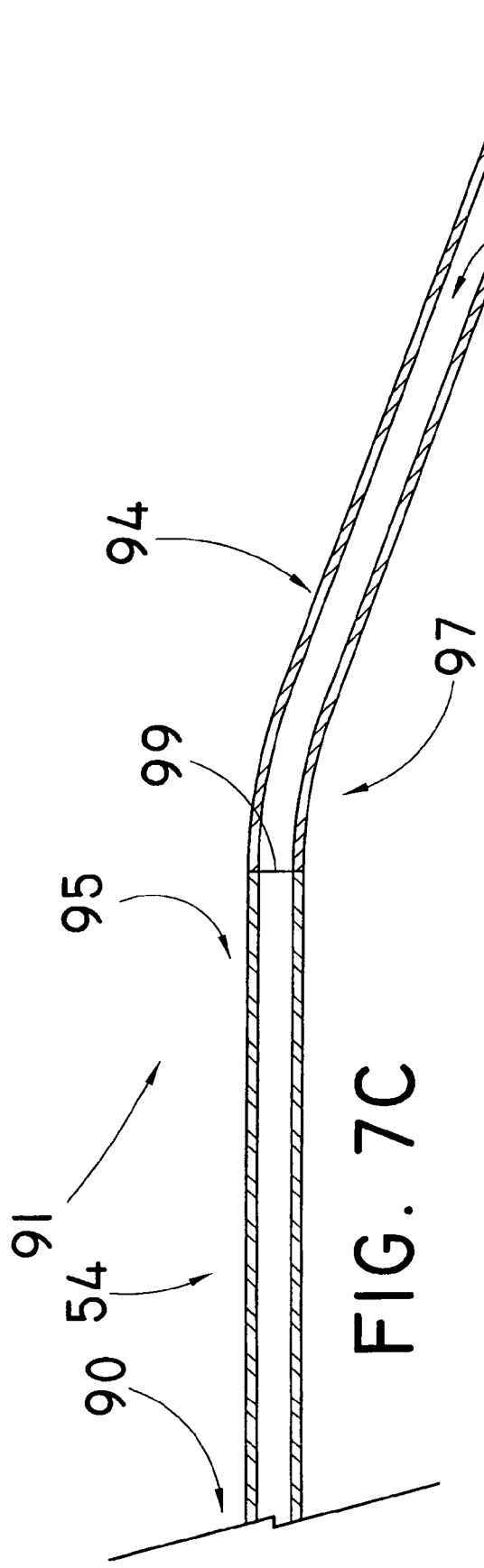
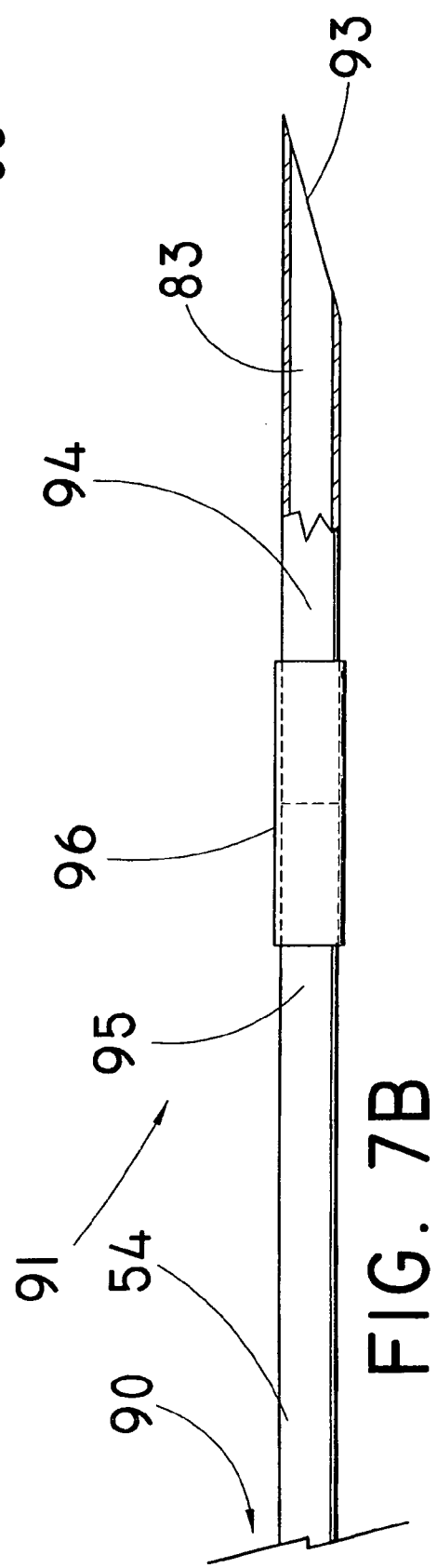

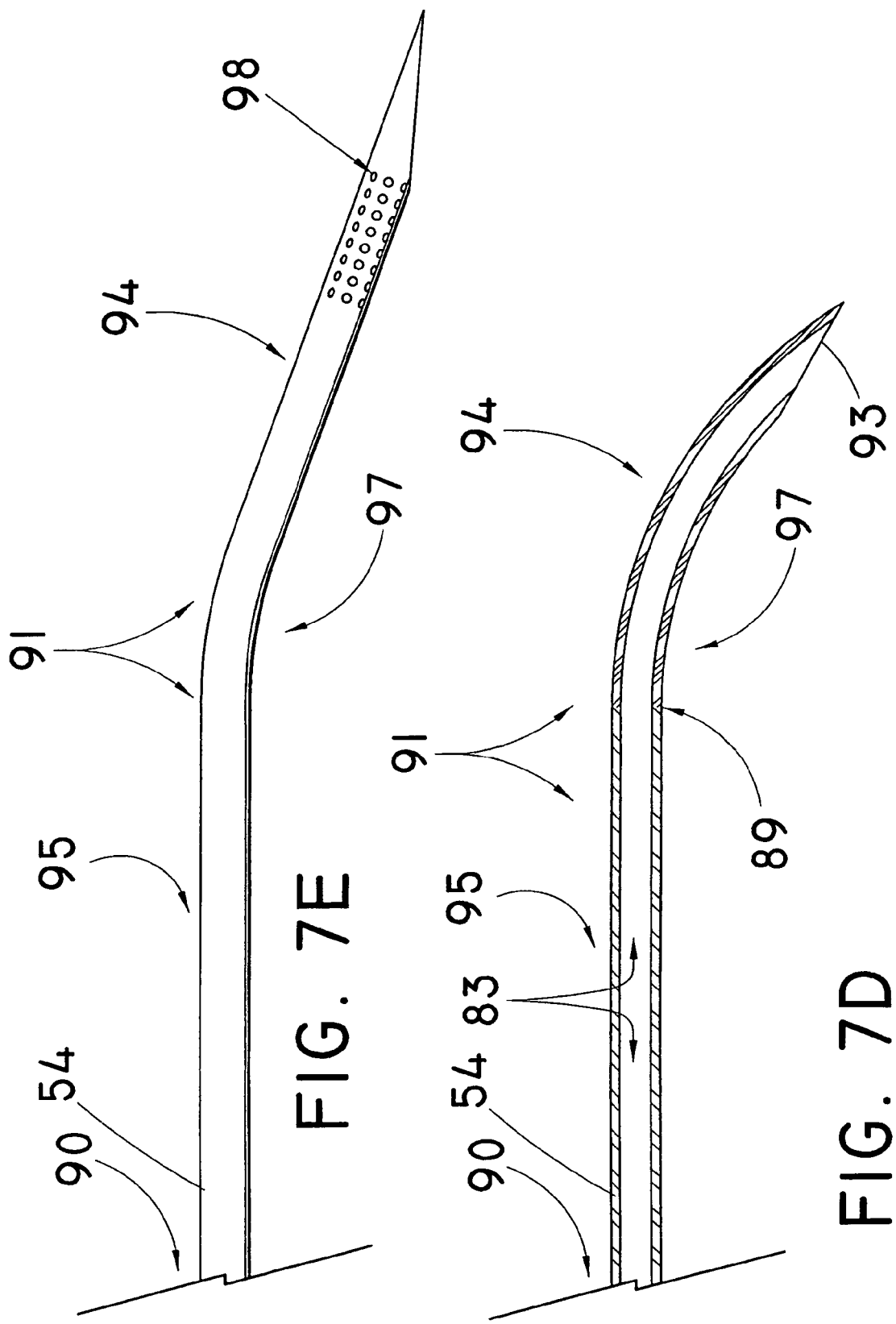

FLEXIBLE ELONGATE SURGICAL NEEDLE DEVICE HAVING A TISSUE ENGAGING SECTION BEING OF GREATER FLEXIBILITY THAN AN INTERMEDIATE SECTION, AND METHODS OF USING THE DEVICE

RELATED APPLICATIONS

The present patent document claims the benefit of the filing date under 35 U.S.C. § 119(e) of provisional U.S. Patent Application Ser. No. 60/636,175, filed on Dec. 15, 2004, which is hereby incorporated by reference in its entirety.

FIELD OF THE INVENTION

The present invention relates to medical devices generally used with an endoscope for delivery of medication and/or for aspiration biopsy to diagnose and stage lesions, and more particularly, to devices, kits, and methods comprising a flexible elongate needle with a distal end for delivery of medication or for removing cells or tissue from, for example, the biliary tree of a patient for biopsy.

BACKGROUND OF THE INVENTION

Although not limited in its scope or applicability, the present invention relates generally to a device used with an endoscope, and more particularly the device that may be used, by way of illustration and not by way of limitation, for delivery of medication and/or for taking a biopsy of a lesion, tumor, neoplasm or other object of, for example, a biliary tree that includes bile ducts, cystic ducts, hepatic ducts, common bile duct, pancreatic ducts, and other channels associated therewith.

Bile Duct

Bile is a fluid made in the liver and then concentrated and stored in the gallbladder, which is a pear-shaped organ found below the liver. Bile helps with digesting fat in the small intestine. The way that bile moves from the liver to the intestine is via a bile duct.

In general terms, the bile duct is a tube about 4 to 5 inches long in the average adult that connects the liver, gallbladder, and pancreas to the small intestine, the part of the digestive tract that is located between the stomach and the large intestine. In more specific terms, the bile duct is sometimes known as a biliary tree (a network of bile duct tubes, cystic ducts, hepatic ducts, common bile duct, pancreatic ducts, and other channels associated therewith). The bile duct begins in the liver as many small channels that gather bile from the liver cells. These small channels all join into one tube (the hepatic duct). About one-third along the length of the bile duct, the gallbladder is attached thereto by a small duct called the cystic duct. The combined duct is called the common bile duct. The end of this part of the bile duct is what empties into the earliest part of the small intestine, next to where the pancreatic duct also enters the small intestine.

At times, problems may develop within the bile duct, whereby bile duct exploration becomes a necessary medical procedure. One example of bile duct exploration is a procedure used to see if a stone or some other obstruction is blocking the flow of bile from the liver and gallbladder to the small intestine. This can cause bile to back up into the liver and result in jaundice or infections, which may require emergency surgery to remove the stone or blockage.

Another example of bile duct exploration is with diagnosing the bile duct, bile duct neoplasms, and bile duct tumors for cancer. Bile duct cancer can develop in any part of the bile duct and, based on its location, is typically divided into three groups. About two-thirds of bile duct cancers develop at the part of the hepatic duct where the bile ducts have joined and are just leaving the liver. These are called perihilar cancers and sometimes Klatskin tumors. About one-fourth of bile duct cancers are found in the common bile duct nearest the intestine. These are called distal bile duct cancers. Rounding out the remaining percentage of bile duct cancers is the third group, which includes cancers that develop in the small bile duct branches inside the liver and are called intrahepatic (i.e., inside the liver) bile duct cancers.

Not all bile duct tumors are cancerous. For instance, bile duct hamartomas and bile duct adenomas are benign tumors. Once the patient presents with symptoms, however, bile duct tumors typically require a prognosis to determine whether they are cancerous or benign. For instance, a physician or other healthcare professional (collectively, "physician") may conduct a history and a physical examination to check for signs of disease, such as lumps, jaundice, and anything else that seems unusual. The physician may also perform liver function tests, in which a blood sample is checked to measure the amounts of certain substances released in the blood by the liver. Another procedure involves the use of a CT scan, whereby a dye is injected into a vein or swallowed to help the organs and tissues show up more clearly in pictures made by a computer that is linked to an X-ray machine. An MRI (magnetic resonance imaging) is still another procedure. This procedure uses a magnet, radio waves, and a computer to make a series of pictures of areas inside the body. Two other examples include the use of ultrasound and biopsy.

Ultrasound

Ultrasound is a familiar medical procedure and is commonly used, for example, in obstetrics and gynecology. Ultrasound utilizes transducers, often called probes that both generate and receive high-energy sound waves (ultrasound) with the use of quartz crystals by utilizing a principle called the piezoelectric effect. When the crystals receive an electric current, the crystals change shape and produce the high-energy sound waves that travel outward to the tissue. Conversely, when sound or pressure waves bounce off internal tissues or organs (make echoes) they hit the crystals, which then emit electrical currents. Therefore, the same crystals can be used to send and receive sound waves. A central processing unit processes the electrical currents emitted by the crystals as a result of the echoes, and the echo patterns are shown on a screen of an ultrasound machine to form a computer picture of body tissues called a sonogram.

Biopsy

Biopsy is the removal of cells or tissues for examination so they can be viewed under a microscope to check for signs of cancer. When a physician removes only a sample of tissue, then the procedure is known as an incisional biopsy or core biopsy. When the physician removes an entire lump or a large area, then the procedure is known as an excisional biopsy. When a sample of tissue or fluid is removed with a needle, the procedure is known as a needle biopsy or fine-needle aspiration.

In a fine-needle aspiration procedure, a fine sterile needle is inserted into the bile duct and guided, typically by employing ultrasound technology, to the tumor location for biopsy. Aspiration is a suction process that removes the cells or tissue sample to be examined under a microscope.

The types of needles that physicians commonly use for biliary aspiration biopsy are a long beveled needle, a ball-tipped needle, or a dimpled needle. Each of these needles is constructed in the axial direction from a relatively homogenous material. In other words, each needle may be made of a substantially consistent composition or material along the length of the needle. For example, the entire needle may be formed of the same material, such as surgical stainless steel or similar alloy. Because of the tortuous paths that the needle must navigate, it would be desirable to have a device comprising a needle with additional flexibility at its distal end, as taught herein.

SUMMARY OF THE INVENTION

A surgical needle is provided. In one embodiment, the needle is elongated with a proximal end and a distal end. The distal end is flexible and has a tissue engaging section and an intermediate section. The tissue engaging section has greater flexibility than the intermediate section.

In another embodiment, a surgical needle device is provided for delivering medication and/or removing tissue. The device has an elongate sheath with openings at a proximal end and a flexible distal end, the openings defining a channel. An elongate needle having openings at proximal and distal ends defining a channel is slideably positioned between first and second positions within the sheath channel. The needle distal end is flexible and comprises a tissue engaging section and an intermediate section, whereby the tissue engaging section has greater flexibility than the material forming the intermediate section. The device has a stationary member and an adjustable member moveable relative to the stationary member, each member having openings at proximal and distal ends defining a channel therebetween. The proximal end of the sheath is secured at or near the stationary member distal end, and the proximal end of the needle is configured to be secured to the adjustable member whereby the adjustable member is capable of moving the needle between the first and second positions.

The present invention also comprises kits useful for delivering medication and/or a needle biopsy of the biliary tree of a patient. In one embodiment, the kit comprises a main body having a stationary member and adjustable member moveable between first and second positions relative to the stationary member. The adjustable member has a proximal opening and the stationary member has a distal opening, whereby the openings define a main body channel. There is an elongate sheath having proximal and distal ends with openings defining a sheath channel, whereby the sheath proximal end is configured to be secured at or near the stationary member distal end. Also, there is an elongate needle slideably positioned axially within the sheath channel. The needle has a proximal end and flexible distal end and openings at the proximal and distal ends define a needle channel, whereby the proximal end is configured to be secured to the adjustable member and moveable between first and second positions. The needle distal end further comprises a tissue engaging section having greater flexibility than an intermediate section. The kit also includes a syringe for delivering medication and/or a source of negative pressure configured to be secured to the adjustable member proximal opening in communication with the main body channel.

Methods of performing a needle surgery are also provided. In one embodiment, a needle device is provided that has an elongate surgical needle moveable between first and second positions, whereby the needle has a proximal end and a flexible distal end comprising a tissue engaging section and an intermediate section. The tissue engaging section has greater flexibility than the intermediate section. The needle device is configured to be connected to a syringe. The needle distal end is introduced to a surgical site. The first and second positions are set for the elongated needle. The needle distal end tissue engaging section is advanced to the surgical site. A syringe is prepared and connected to the device for delivering surgical procedures, such as for delivering medication and/or for providing aspiration to the surgical site.

BRIEF DESCRIPTION OF THE DRAWINGS

FIG. 1 provides a plan view of various components of a kit according to one embodiment of the present invention.

FIG. 2 provides a perspective side view, partially exploded, of a syringe for delivering medication and/or negative pressure according to one embodiment of the present invention.

FIG. 3 is a longitudinal sectional side view of FIG. 2.

FIG. 4 provides a perspective side view, broken away, of a main body of a device according to one embodiment of the invention.

FIG. 5 is a longitudinal sectional side view, further broken away, of FIG. 4.

FIG. 7B provides a perspective partially longitudinally sectioned side view, broken away, of an alternative embodiment of a needle according to the invention.

FIG. 7C provides a perspective longitudinally sectioned side view, broken away, of another embodiment of a needle according to the invention.

FIG. 7D provides a perspective longitudinally sectioned side view, broken away, of an alternative embodiment of a needle according to the invention.

FIG. 7E provides a perspective side view, broken away, of an still another embodiment of a needle according to the invention.

DETAILED DESCRIPTION OF EMBODIMENTS

Figure 6:
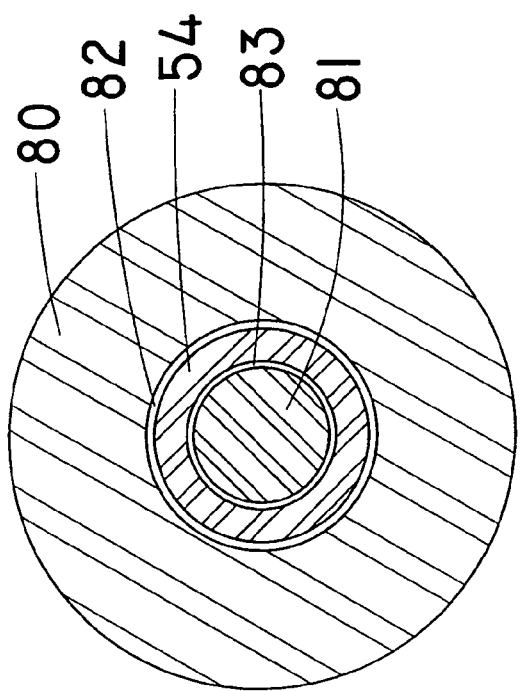
FIG. 6 provides a cross sectional view taken along lines 6-6 of FIG. 4.

This invention relates generally to medical devices and, in particular, to a surgical needle device for delivering medication and/or performing an aspiration biopsy and, more particularly, to a device that includes a needle having a distal end that includes a tissue engaging section being of greater flexibility than an intermediate section, wherein the needle may be used with an endoscope, through an endoscope accessory/working channel, or through an external accessory channel device used with an endoscope. By way of background, a conventional endoscope generally is an instrument with a light source and image sensor for visualizing the interior of an internal region of a body. A wide range of applications have been developed for the general field of endoscopes including, by way of example, the following: arthroscope, angioscope, bronchoscope, choledochoscope, colonscope, cytoscope, duodenoscope, enteroscope, esophagogastro-duodenoscope (gastroscope), laparoscope, larynogoscope, nasopharyngoneproscope, sigmoidoscope, thoracoscope, utererscope, and/or a working channel thereof and/or any external accessory channel device used with any of the foregoing (collectively, "endoscope").

For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, with, contain(s) and the variants thereof are intended to be open ended transitional phrases, terms, or words that do not preclude the possibility of additional steps or structure.

In FIG. 1, an illustrative embodiment of a kit for a surgical needle device 10 containing various components of one embodiment of the present invention is provided. As illustrated in FIG. 1, the surgical needle kit 10 of the embodiment comprises a main body 11. The surgical needle kit 10 further includes a needle assembly 51 and a syringe 15. Optionally, the surgical needle kit 10 may be shipped and/or stored in any suitable packaging 12 configured for containing the kit 10 such as, by way of example and not by way of limitation, a plastic material, Styrofoam, inflation device, or paper container having recesses capable of receiving the main body 11, the needle assembly 51, and the syringe 15 and/or an envelope or box having at least one inner compartment for receiving the kit 10. By way of further examples, packaging 12 may comprise a variety of materials including but not limited to polyurethane, polyethylenes, polypropylenes, polyethylene terephthalates, polyvinyl chlorides, a plastic composite, and/or paper.

Syringe

FIGS. 2 and 3 provide a view of a syringe 15, whereby the term "syringe" includes any device or source for delivering medication and/or for providing a source of negative pressure. While the discussion below addresses a syringe 15 for providing a negative pressure, the discussion should be understood to apply also to a source for delivering medication whereby the negative pressure would be replaced with medication. Also, the syringe 15, as used herein and throughout to describe embodiments of the invention, may be any instrument, device, machine, or apparatus comprising a mechanical, electrical, electromechanical, pneumatic, hydraulic, or combination thereof for delivering medication and/or for providing a source of negative pressure.

FIG. 3 shows one embodiment of the syringe 15 for biopsy aspiration used in withdrawing cells or tissue and is not limited to the syringe shown or to a conventional syringe. In the embodiment shown in FIG. 3, the syringe 15 includes a barrel 20, a plunger assembly 27, and a passageway 28 for passing the cells or tissue into the barrel 20 or delivering medications from the barrel 20.

The barrel 20 may be any device having a reservoir for an aspiration vacuum and/or for collecting the cells or tissue for biopsy and/or for delivering medication. In one embodiment of the barrel 20, the barrel 20 may have proximal and distal openings 21, 22, respectively, at first and second ends 23, 24, respectively, and defining a chamber 25 with an inside surface 26. As is conventional, "distal" means away from the physicion when the device is inserted into a patient, while "proximal" means closest to or toward the physicion when the device is inserted into a patient. The chamber 25 is any structure capable of serving as a reservoir for an aspiration vacuum and/or a reservoir for retaining biopsy cells or tissue and/or for delivering medication. The chamber 25 may be of varying lengths and dimensions, and in one embodiment the chamber 25 optionally may be by way of example approximately 10 cubic centimeters, although the volume may be more or less if so desired.

The syringe 15 further comprises a plunger assembly 27 at its first end 23 and a passageway 28 at its second end 24. The plunger assembly 27 may be any structure used for creating an aspiration vacuum in the chamber 25 and/or expelling medication. In describing one embodiment of the plunger assembly 27 by way of example only, the plunger assembly 27 includes an elongated plunger rod 29 with proximal and distal ends 30, 31, respectively. At the proximal end 30 is an optional disc-shaped flange 32 for allowing the physician to apply the force necessary to move the plunger rod 29 slidably with respect to the barrel 20. At the distal end 31 of the plunger rod 29 is a flexible stopper 33. Optionally, the flexible stopper 33 may be made from a material that is different from the material comprising the plunger rod 29. The stopper 33 may be any structure configured to form a suitable seal with the inside surface 26 of the barrel chamber 25. Examples of a suitable stopper 33 include but are not limited to a gasket, O-ring, and/or the like.

Intermediate the proximal and distal ends 30, 31, respectively, of the plunger rod 29 are an optional plurality of elongated recesses 34 and one or more optional elongated plunger locks 35. The term "intermediate" is intended to mean between, though not necessarily equidistant to, the most distal tip of the distal end 31 and the most proximal tip of the proximal end 30 of the plunger rod 29. The recesses 34 act as a pathway for longitudinal motion of the locking element relative to the plunger rod assembly.

The optional plunger locks 35 extend laterally outward and transverse to the plunger rod longitudinal axis so as to avoid unintentional axial sliding of the plunger rod 29. The optional plunger locks 35 are joined to the plunger rod assembly attachment points 36 at or near the distal and proximal ends 30, 31, respectively, of the plunger rod 29. Intermediate the attachment points 36, the plunger locks 35 may flare outwardly with respect to the longitudinal axis of the plunger rod 29 so as to form a V-shaped body 37 that abuts a corresponding flange 38 at a proximal opening 21 of the barrel 20 to facilitate handling and positioning of the syringe assembly and to maintain the relative position of the barrel 20 with respect to the plunger rod 29 during evacuation and filling.

Turning to the second end 24 of the barrel 20, according to one illustrative embodiment of the barrel 20, the barrel has a passageway 28. The term "passageway" is understood to be any lumen, chamber, channel, opening, bore, orifice, flow passage, duct, or cavity for the conveyance, regulation, flow, or movement of fluids and/or gases. In one embodiment, the passageway 28 is in distal communication with an optional stopcock assembly 39. Optionally, the stopcock assembly 39 includes a proximal spacer 40 defining a tube that may have rigid outer and inner diameters. The diameters may be any suitable dimension, and examples include an outer diameter of 0.410 centimeters and an inner diameter of 0.075 centimeters.

In distal communication with the optional tubular proximal spacer 40 is an optional stopcock 41. A stopcock 41 is any structure suitable for stopping or regulating flow through the passageway 28. In one embodiment, the stopcock may be a one-way swivel universal male luerlock. In distal communication with the stopcock 41 may be a distal spacer 42 defining a tube that optionally may have a rigid outer diameter of 0.410 centimeters and an inner diameter of 0.075 centimeters. The distal spacer 42 has a distal fitting 43 defining an opening 44, whereby the distal fitting 43 may be a Luer slip that connects to a proximal main body fitting 45.

The syringe 15 is easily constructed from the component parts thereof. The syringe barrel 20 of the present invention may be constructed of a wide variety of thermoplastic materials such as polypropylene, polyethylene and combinations thereof. Similarly, thermoplastic materials such as polypropylene, polyethylene and polystyrene are suitable materials for the elongated plunger rod 29 and flexible stopper 33. A wide variety of materials such as natural rubber, synthetic rubber and thermoplastic elastomers are suitable for the stopper if the stopper is manufactured as a separate component or made by a two-shot molding process or the like. The choice of stopper material will depend on compatibility with the cells and tissues being extracted and the barrel material and thickness since the stopper must form a seal with the inside surface of the barrel. Furthermore, FIGS. 1-3 describe an embodiment of a syringe 15 which may be, by way of example and not by way of limitation, a hypodermic syringe or any suitable instrument, machine, device, or apparatus used to inject fluids into the body or draw fluids from the body.

Main Body

FIGS. 4 and 5 show a main body 11 for use with or independent of a surgical needle device 54. The main body 11 includes an actuator 50 and a needle assembly 51 (see FIG. 4).

An actuator 50 may be any device for moving, displacing, or controlling, directly or indirectly, a needle 54. For example, the actuator 50 may be mechanical, electrical, electromechanical, pneumatic, hydraulic, or a combination thereof.

FIGS. 4 and 5 show one illustrative embodiment of an actuator 50. In that embodiment, the actuator 50 includes a stationary member 52 and an adjustable member 53 that moves relative to the stationary member 52 between a first position 110 and a second position 120 for actuating a needle 54 relatively corresponding between first and second positions. Optionally, the stationary or adjustable members 52, 53, respectively, may be adapted to connect to a syringe 15 (whereby the term "syringe" includes any mechanical, electrical, electromechanical, pneumatic, and/or hydraulic device, apparatus, machine, instrument, or source for aspirating a biopsy site or delivering medication to a surgical site). In the embodiment of FIGS. 4 and 5, the adjustable member 53 is adapted to connect to the syringe 15, as explained below.

By way of illustration and not by way of limitation, in one embodiment the members 52, 53 are tubular and co-axial with co-axial channels, although the members 52, 53 may be any configuration, such as a hand grip-type of handle, that allows or is capable of allowing the adjustable member 53 to move relative to the stationary member 52. In this illustrative embodiment, the adjustable member 53 has proximal and distal ends 55, 56, respectively, optionally having a proximal end opening 62 and distal end opening 49, the proximal and distal ends 55, 56 and/or openings 62, 49 defining a guide channel 57; the tubular stationary member 52 has proximal and distal ends 58, 59, respectively, having an optional proximal end opening 79 and a distal end opening 74 and/or 78 at or near the distal end 59, the proximal and distal ends 58, 59 and/or openings 79, 74, 78 defining a guide channel 60 there between; and the adjustable member 53 slideably fits over a portion of, and is axially slideable relative to, the stationary member 52. The adjustable member channel 57 is configured to be in fluid communication with—directly or indirectly through intervening parts—the stationary member channel 60, wherein the term "fluid communication" and variants thereof are not used lexicographically but instead are used to describe embodiments of the invention such that the channels 57, 60 are configured to allow conveyance, regulation, flow, or movement of bodily fluids, medication, negative or positive pressure, and/or gases therebetween. As used herein, the term "channel" is understood to be any lumen, chamber, channel, opening, bore, aperture, orifice, flow passage, passageway, cavity, or cannula that facilitates the passage, conveyance, ventilation, flow, movement, evacuation, or regulation of fluids or gases or the passage or movement of an instrument or component.

Positioned within the adjustable member 53 guide channel 57 of this illustrative embodiment is a needle hub 61. The needle hub 61 may be any structure configured to secure, directly or indirectly, a non-tissue engaging portion of a needle (e.g., the proximal end 90 of the needle 54) for moving the needle 54 between first and second positions as the adjustable member moves between first and second positions 110, 120, respectively, and that has a passageway for receiving a stylet (discussed later). In this embodiment, the needle hub 61 is secured to a proximal end of a needle. Furthermore, the hub 61 may be positioned at, near, or intermediate to the proximal or distal ends 55, 56 of the adjustable member 53. In one embodiment, the hub 61 is positioned at or near the proximal end 55, such as to the main body fitting 45, or in another embodiment the needle hub 61 may be the proximal main body fitting 45 or integral therewith. The hub 61 may secure a non-tissue engaging proximal end 90 of the needle 54 by any suitable means, such as by crimping, welding, soldering, brazing, adhesives, or by connector means whereby the proximal end of the needle has a female member, such as a ball, bearing, or thread, and the hub has a male member, such as a socket or bore into which the female member is secured.

FIG. 5 shows that one embodiment of the adjustable member 53 proximal end 55 may further comprise a proximal main body fitting 45 having a guide channel opening 62 for connecting the syringe 15. In one embodiment, the main body fitting 45 connects the distal spacer 42 (see FIG. 3) of the syringe 15 as previously described. The main body fitting 45 forms a suitable seal with the syringe 15 for aspiration of the biopsy site and/or delivery of medication to the surgical site.

The adjustable member 53 is axially slideable between first and second positions 110, 120, respectively, relative to the stationary member 52 for extending and retracting the needle distal end tissue engaging section 94 (see FIG. 4). FIG. 5 shows that the adjustable member 53 optionally has one or more joints 63 on the inside surface 64 to slideably engage a corresponding groove 65 on an outside surface 66 of the stationary member 52. The joint 63 and groove 65 help to guide the adjustable member 53 along a substantially straight path relative to the stationary member 52 and maintain proper alignment of the adjustable member 53 and stationary member 52 to reduce shifting or rotation of the adjustable member 53 relative to the stationary member 52 as the adjustable member moves between first and second positions. The joint 63 and groove 65 minimize kinking of the needle 54 as the needle moves between first and second positions.

As shown in FIGS. 4 and 5, the stationary member 52 has proximal and distal restraints 67, 68, respectively, for stopping the adjustable member from sliding off the stationary member proximally or distally respectively. For instance, in one embodiment the proximal restraint 67 may be a flange that is large enough circumferentially (or optionally any other suitable protrusion) sufficient to make contact with the distal end 56 of the adjustable member 53 to stop the adjustable member from sliding proximally off the stationary member. The distal restraint 68 may be any slideable means having a protrusion or a circumference that is large enough for stopping the adjustable member from sliding distally off the stationary member. In one illustrative embodiment, the distal restraint 68 is a thumbscrew ring that slideably secures the outside surface 66 of the stationary member 52, and has a ring 69 with a threaded bore 70 and a thumbscrew 71 that fits the bore 70. Optionally, the distal restraint 68 has one or more joints 72 to slideably engage a corresponding groove 65 on an outside surface 66 of the stationary member 52. In still another embodiment, the distal restraint 68 may be any flange or protrusion formed at or near stationary member the distal end 59 sufficient to block distal movement of the joint 72 and/or the joint 63.

According to FIG. 4, the stationary member outside surface 66 may have optional markings 73 for setting the desired length of distal movement of the adjustable member 53. The distal restraint 68 is slideably moveable to a mark on the outside surface 66 of the stationary member 52 corresponding to the desired second position 120 of the adjustable member 53. Therefore, the distance between the first and second positions 110, 120, respectively, of the adjustable member 53 is variable and corresponds relatively to the desired extension and retraction of the needle 54. At the distal end 59 of the stationary member 52, there is a distal opening 74 for passageway of the needle 54 and needle sheath 80 (see FIGS. 4 and 5).

In one embodiment, the distal end 59 of the stationary member 52 further comprises an optional female adaptor 75 containing a channel 60 and distal opening 74 (see FIG. 5). An optional distal male adaptor 76 containing a channel 77 and distal opening 78 connects to the female adaptor 75 by any suitable means, such as a threading arrangement, glue, or adhesives. The optional male adaptor 76 may serve as a spacer and/or a distal restraint 68 for stopping the adjustable member from sliding off the stationary member proximally or distally respectively.

Needle Assembly

As shown in FIG. 1, the device further comprises a needle assembly 51, which includes a needle 54 having a tissue engaging section 94 and an intermediate section 95 arranged in an axial direction, the sections having different flexibility such that the tissue engaging section 94 has greater flexibility than the intermediate section 95. The needle assembly 51 also may comprise an optional needle sheath 80 and an optional stylet 81 (not shown).

In describing embodiments of the invention, the tissue engaging section 94 and intermediate section 95 are arranged in an axial direction. In other words, the tissue engaging section 94 extends lengthwise and distally from the intermediate section 95. As used herein and throughout to describe embodiments of the invention, the axial direction includes an arrangement whereby the tissue engaging section 94 and intermediate section 95 may be relatively straight or may at times even be curved relative to each other because, as explained below, the tissue engaging section 94 and intermediate section 95 are flexible and the tissue engaging section 94 optionally has a preformed bend. Furthermore, the tissue engaging section 94, which extends distally from the intermediate section 95, may be by operatively coupled to the intermediate section 95 by mechanical means, chemical means, and/or by forming the sections integrally.

The terms "operatively coupling," "operatively coupled," "coupling," "coupled," and variants thereof are not used lexicographically but instead are used to describe embodiments of the invention having a point, position, area, volume, or configuration at which a tissue engaging section 94 (having greater flexibility than the intermediate section 95) and the intermediate section 95 are mechanically, chemically, and/or chemical-mechanically bonded, joined, adjoined, connected, associated, united, mated, interlocked, conjoined, fastened, held together, clamped, crimped, friction fit, press fit, or wedged directly or indirectly (e.g., with a crimp sleeve, soldering, brazing, welding, glue, adhesives, resins, chemical bonding materials or combinations thereof and the like). In one embodiment, the tissue engaging section 94 and intermediate section 95 are formed of different materials a first material is more flexible than a second material, and the tissue engaging section 94 comprises the first material whereas the intermediate section 95 comprises the second material. Optionally, the sections 94, 95 may be formed from like materials having the same or substantially similar cross sectional area but have been treated, laminated, manufactured, and/or shaped such that the tissue engaging section 94 has greater flexibility than the intermediate section 95. When the sections 94, 95 are operatively coupled by being formed integrally, the sections 94, 95 may be formed integrally by any suitable means such as, by way of example and not by way of limitation, extruding the tissue engaging section 94 using a first material (of greater flexibility or treated to have greater flexibility than a second material) and then extruding the intermediate section 95 using a second material (of lesser flexibility or treated to have lesser flexibility than the first material). Alternatively, the sections 94, 95 may be operatively coupled by being formed integrally by, for example, extruding like materials to form sections 94, 95 having similar cross sectional areas and then treating, laminating, manufacturing and/or shaping the sections 94, 95 to make the tissue engaging section 94 more flexible than the intermediate section 95.

It should be understood that a region where the tissue engaging section 94 and the intermediate section 95 are operatively coupled may have a gradual change in the materials of different flexibility. In other words, the region where the distal end intermediate section 95 axially segues into the distal end tissue engaging section 94 may exhibit flexibility properties different from either the materials comprising the tissue engaging section 94 and/or the intermediate section 95. In other words, gradual changes within tolerance are contemplated.

Figure 7A:
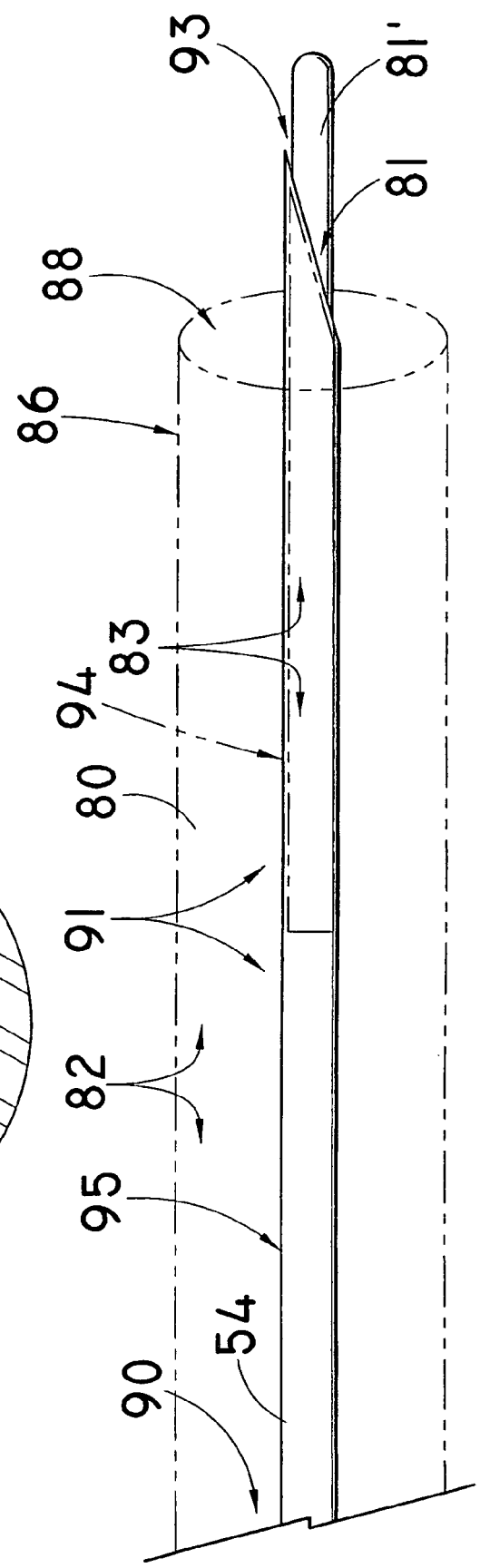
FIG. 7A provides a perspective side view, broken away, of a needle assembly according to one embodiment of the invention.
Figure 8:
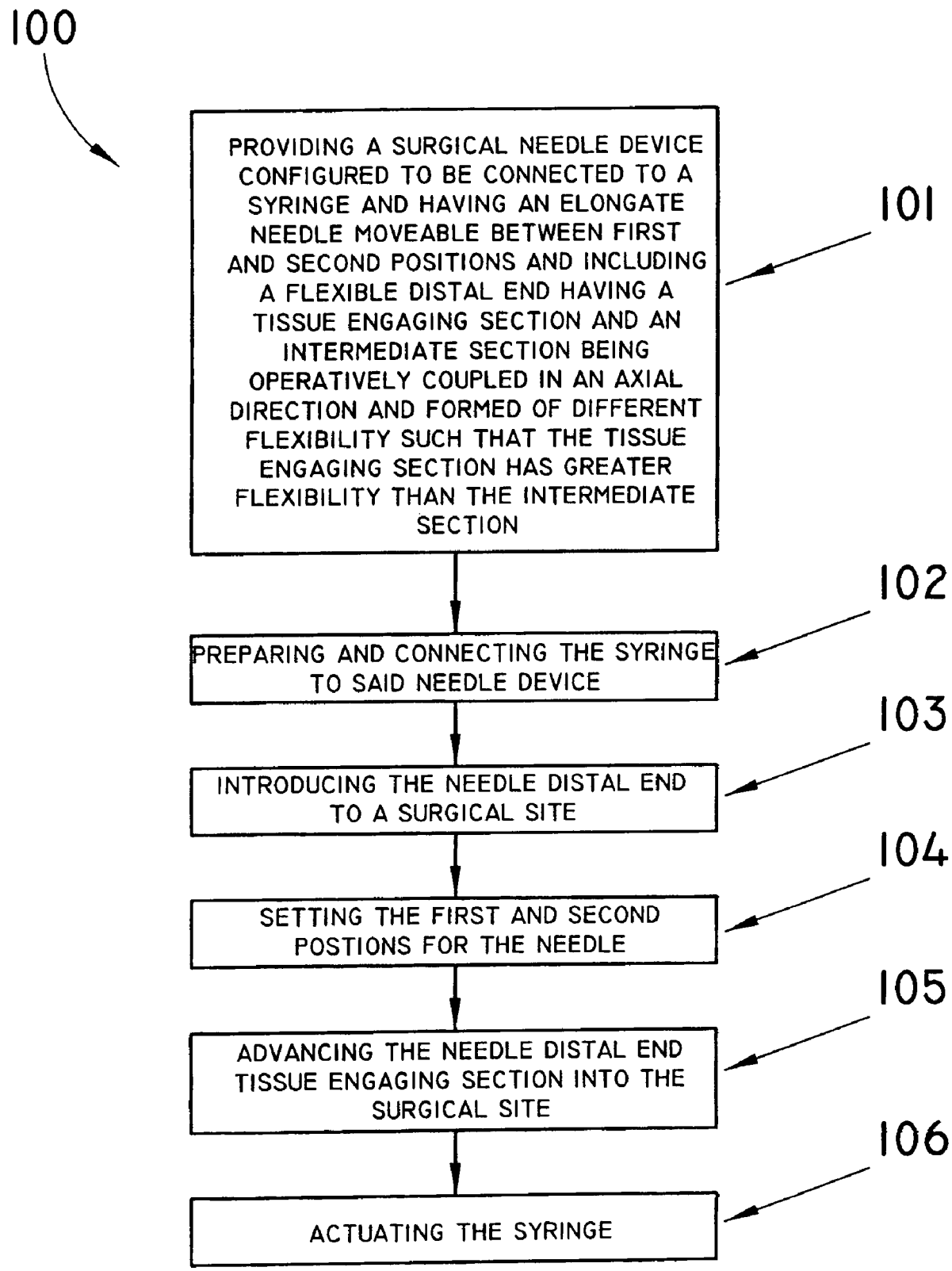
FIG. 8 is a block diagram illustrating a method of the invention.

FIGS. 5, 6, and 7A show the optional stylet 81, which may be any stiffening member for maintaining patency of the needle sheath 80 and/or the needle 54 during storage, shipping, and/or use. In one embodiment, the stylet 81 is an elongated slender body such as a wire, rod, shaft, or cable configured to be capable of being inserted into the proximal main body guide channel opening 62, extending through the adjustable and stationary member channels 57, 60, respectively, and within both a sheath channel 82 and needle channel 83 in the sense that the needle 54 is within the needle channel 83 that is within the sheath channel 82. The optional stylet 81 in one embodiment comprises a length similar to the length of the needle 54. In one embodiment, the stylet 81 optionally extends from a proximal end 84 at or near the proximal end 90 of the needle 54 to a distal end 81' at or near the distal end 91 of the needle. In one embodiment, the stylet proximal end 84 is a proximal thumb piece used by the physician to advance or retract the stylet, and optionally to remove the stylet for connecting the syringe to the adjustable member.

FIGS. 5, 6, and 7A further show the optional sheath 80. In general terms, the optional sheath 80 is any covering having a channel 82 configured for and capable of slideably receiving the tissue engaging section 94 and/or the intermediate section 95 of the needle 54, which needle 54 also includes a channel 83. The optional needle sheath 80 has proximal and distal ends 85, 86, respectively, and corresponding openings 87, 88 defining the channel 82. The sheath may be formed of any suitable material such that the distal end is flexible. In one embodiment, the proximal and distal ends 85, 86 of the sheath 80 are flexible, while in another embodiment only the distal end 86 is flexible. For example, suitable materials include surgical stainless steel or biologically compatible metals, polymers, plastics, alloys (including super-elastic alloys), or composite materials that are either biocompatible or capable of being made biocompatible. The optional sheath 80 is relatively elongate (long). The overall length of the sheath may vary, however, and in one embodiment the length may be in the range of 100 to 250 cm, although the length of the sheath may be shorter or longer, as desired. In yet another embodiment, the length of the sheath, as in use for a biliary biopsy or to deliver medicine to the biliary region, may be in the range of 200 to 215 cm, although the length of the sheath may be shorter or longer.

The device may be used in the passageways of an aorta, artery, bile duct, blood vessel, bronchiole, capillary, esophagus, fallopian tube, heart, intestine, trachea, ureter, urethra, vein, and other locations in a body (collectively, "vessel") to name a few. Given the configuration of vessels and vessel passageways to be navigated, a mostly "tubular" sheath (as one embodiment) may be better tolerated by the patient to minimize pain and discomfort. The term "tubular" in describing this embodiment includes any tube-like, cylindrical, elongated, shaft-like, rounded, oblong, or elongated structure or member that comprises a guide channel 82. Thus, the outer diameter of the sheath may vary. In one embodiment, the outer diameter is approximately 0.28 cm, although the outer diameter of the sheath may be greater or lesser.

The sheath proximal end 85 (see FIG. 5), which may be flexible or rigid, is secured to the main body 11. In one embodiment, the sheath proximal end 85 is received in opening 74 of the stationary member distal end 59. In an embodiment having a distal male adaptor 76, the sheath proximal end 85 may be received in the male adaptor opening 78. The sheath proximal end 85 may be secured by any suitable means, such as by crimping, welding, brazing, glue, or adhesives. In an alternative embodiment, it may be secured by a mechanical connector means whereby the proximal end has a male member, such as a ball, bearing, thread, or flange (all containing a proximal opening 87 and channel 82), and the stationary member distal end 59 or distal male adaptor 75 have a female member, such as a socket or bore into which the male member is secured. In yet another embodiment, a combination of mechanical connector means, crimping, welding, brazing, glue, and adhesives are utilized.

FIG. 7A shows an embodiment of a needle assembly 51 according to an embodiment of the device having a needle 54 comprising a distal end 91, an optional stylet 81, and an optional sheath distal end 86. For purposes of illustration and viewing for the reader, the radial distance between the needle 54 and the optional sheath 86 is not to scale.

The needle 54 has a proximal end 90 (see FIG. 5), a distal end 91 (see FIGS. 7A-7E), and corresponding openings 92, 93 (see FIGS. 5, 7A, 7B, 7C, and 7D) defining a channel 83 (see FIGS. 6, 7A, 7B, and 7D). The distal opening 93 may be any suitable configuration, as in beveled, oblong, oblique, chamfered, rounded, ball-tipped, or dimpled. The needle 54 is relatively long (elongated). However, the overall length of the needle 54 may vary. In one embodiment, the length of the needle 54 may be in the range of 100 to 250 cm, although the length of the needle may be shorter or longer. In yet another embodiment, the length of the needle, as in use for a biliary biopsy or to deliver medicine to the biliary region, may be in the range of 200 to 215 cm, although the length of the needle may be shorter or longer. Likewise, the outer and inner diameters of the sheath may vary. In one embodiment, the outer diameter is approximately 0.15 cm, although the outer diameter of the needle may be greater or lesser. In one embodiment, the inner diameter is approximately 0.075 cm, although the inner diameter of the needle may be greater or lesser. In one embodiment, the proximal and distal ends 90, 91 of the needle 54 are flexible, while in another embodiment the distal end 91 is flexible.

The needle 54 is moveable between first and second positions (e.g., 110 and 120, respectively) relative to the movement of the adjustable member 53 between first and second positions 110, 120, respectively, as previously described (see FIG. 4). In general, the first position 110 is proximal to the second position 120. In another embodiment, first and second positions 110, 120, respectively, correspond to retracted and extended, respectively. In still another embodiment, the first and second positions 110, 120, respectively, correspond to tissue non-engaging and tissue engaging positions, respectively, for delivering medication to a surgical site and/or aspiration to a surgical biopsy site. In yet another embodiment, the first position 110 means that the opening 93 of the tissue engaging section 94 of the needle distal end 91 is fully protected from the body vessel by the sheath distal end 86, while the second position 120 means that the opening 93 of the tissue engaging section 94 of the needle distal end 91 is not fully protected by the sheath distal end 86. In still another embodiment, the first position 110 means that the opening 93 of the tissue engaging section 94 of the needle distal end 91 is proximal to the distal opening 88 of the sheath distal end 86, while the second position 120 means that the opening 93 of the tissue engaging section 94 of the needle distal end 91 extends beyond (distal to) the distal opening 88 of the sheath distal end 86. In yet another embodiment, first and second positions 110, 120, respectively, may correspond generally to the movements of the adjustable member 53 (or initial and final positions of the distal restraint 68) as previously described. As can be seen, the first and second positions are variable.

The proximal end 90 is a non-tissue engaging end of the needle 54 (see FIG. 5). In one embodiment, the proximal end 90 is secured to the main body, directly or indirectly with intervening parts, by the adjustable member needle hub 61. Optionally, the needle hub 61 is secured to a proximal end 90 of a needle 54. Furthermore, the needle hub 61 may be positioned at, near, or intermediate to the proximal or distal ends 55, 56, respectively, of the adjustable member 53. In the embodiment shown in FIG. 5, the needle hub 61 is positioned at the proximal end 55. The needle hub 61 may secure the proximal end 90 of the needle 54 by any suitable means, such as by crimping, welding, soldering, brazing, adhesives, or by connector means whereby the proximal end of the needle has a male member, such as a ball, bearing, or thread, and the hub has a female member, such as a socket or bore into which the male member is secured.

As FIGS. 7A, 7B, 7C, 7D, and 7E show, the distal end 91 of the needle 54 comprises a tissue engaging section 94 and an intermediate section 95 operatively coupled in an axial direction, wherein the tissue engaging section 94 has greater flexibility than the intermediate section 95. Suitable materials for the tissue engaging section 94 and/or intermediate section 95 include surgical stainless steel or biologically compatible metals, polymers, plastics, alloys (including super-elastic alloys), memory-metal alloys, or composite materials that are either biocompatible or capable of being made biocompatible.

The lengths of the tissue engaging section 94 and the intermediate section 95 may vary. In one embodiment, the tissue engaging section 94 is approximately in the range of 1 to 8 cm, while another embodiment is in the range of 2 to 5 cm. Optionally, the intermediate section 95 runs the length of the needle 54 from the needle proximal end 90 to the tissue engaging section 94. In one embodiment, the intermediate section 95 extends proximally from the tissue engaging section 94 to the length of the needle and extends into the main body 11, such as through the distal opening 74 of the stationary member 52 or through the distal opening 78 of an embodiment having a distal male adaptor 76.

The tissue engaging section 94 and intermediate section 95 may be formed of different flexibility in many ways. Optionally, the tissue engaging section 94 and intermediate section 95 may be formed from like materials having the same or substantially similar cross sectional area but having been treated, laminated, manufactured (e.g., at different temperatures, times, or other processes), or shaped geometrically (e.g., centerless grinding, skiving, drilling, laser-cutting, machining, electric discharge machined, stamping, pressing, milling, and/or formed by other known shaping processes) such that the tissue engaging section 94 has greater flexibility than the intermediate section 95.

In one embodiment according to the invention, the tissue engaging section 94 and intermediate section 95 have substantially similar cross sections but are formed of different materials to account for their different flexibility. Owing to the different materials comprising these sections 94, 95, in general the intermediate section 95 is less flexible (more rigid) overall than the tissue engaging section 94. Therefore, the tissue engaging section 95 gives added flexibility to the most distal tip of the distal end 91 of the needle 54.

In one embodiment, the intermediate section 95 may be made comprise a second material such as, by way of example and not by way of limitation, stainless steel or similar alloy, a composite, a polymer, and/or a surgical stainless steel. The tissue engaging section 94 may comprise a first material that is, by way of example and not by way of limitation, a memory-metal alloy such as, for instance only, a nickel titanium alloy or other alloy, composite, or polymer that is made to or is treated to have flexibility similar to a memory-metal alloy such that it is flexible and can accommodate some bending and twisting while still returning to its linear shape. Memory metal is an alloy that can be trained to take on a predetermined shape. There are alloys that may exhibit this characteristic to greater or lesser degree. Some examples of embodiments of memory-metal alloys include copper-zinc-aluminum, iron-manganese-silicon, gold-cadmium, copper-aluminum, and copper-aluminum-nickel. In one embodiment, the memory-metal alloy is a nickel-titanium alloy ("nitinol," an acronym of Nickel Titanium Naval Ordnance Laboratory, where the alloy's properties were discovered). Nitinol is an alloy containing nearly equal numbers of nickel and titanium atoms, and the relative amounts of nickel and titanium can be varied by a few percent.

The tissue engaging section 94 may comprise substantially all memory metal, or may have one or more regions where one region is memory metal while a different region is stainless steel or polymer. For example only and not limiting the invention, in one embodiment of a tissue engaging section 94 that is 5 cm, the proximal 4 cm may be memory metal while the distal 1 cm may be formed from materials traditionally used for biopsy needles, as in stainless steel or similar alloy or a polymer. Conversely in that example, the distal 4 cm may be memory metal while the proximal 1 cm may be formed from materials traditionally used for biopsy needles, as in stainless steel or similar alloy or a polymer.

FIGS. 7A, 7B, 7C, 7D, and 7E show perspective side views, broken away, of alternative embodiments of a needle 54. The tissue engaging section 94 and the intermediate section 95 may be operatively coupled by any suitable means. In FIG. 7A, the tissue engaging section 94 to the intermediate section 95 are operatively coupled directly to each other via mechanically, chemically, and/or chemical-mechanically means. By way of example and not by way of limitation, the tissue engaging section 94 to the intermediate section 95 are bonded, joined, adjoined, connected, associated, united, mated, interlocked, conjoined, fastened, held together, clamped, crimped, swaged, friction fit, press fit, wedged, and/or with glue, adhesives, resins, cyanoacrylates, epoxies, chemical bonding materials, or combinations thereof.

In FIG. 7B, there is a crimp sleeve 96 that secures the tissue engaging section 94 to the intermediate section 95. In describing embodiments of the invention, the crimp sleeve 96 includes any mechanical structure for bonding, joining, adjoining, connecting, associating, uniting, mating, interlocking, conjoining, fastening, holding together, clamping, crimping, swaging, friction fitting, press fitting, or wedging directly or indirectly, as with intervening parts, the tissue engaging section 94 and the intermediate section 95. Optionally, the crimp sleeve 96 further comprises chemically and/or chemical-mechanically structures such as glue, adhesives, resins, chemical bonding materials, or combinations. While FIG. 7B shows the tissue engaging section 94 and intermediate section relatively straight along an axial direction, it should be understood that the sections may also be curved relative to each other, because the tissue engaging section 94 and intermediate section 95 are flexible. Optionally, the tissue engaging section 94 may also comprise a preformed bend 97 as discussed below.

In FIG. 7C, the tissue engaging section 94 and the intermediate section 95 are operatively coupled with a weld 99. Optionally, the weld 99 comprises spot welding, laser welding, TIG, e-beam, radiofrequency, other energy source, and plasma techniques. Alternatively, the weld 99 comprises soldering or otherwise affixing the tissue engaging section 94 and the intermediate section 95 by a passive oxide layer covering, aluminum past flux, or the technique described in U.S. Pat. No. 5,354,623, whose disclosure is incorporated herein by reference.

FIG. 7C also shows an embodiment wherein the needle distal end 91 further comprises an optional preformed bend 97 at or near the tissue engaging section 94. A bend 97 can be a curve, and a curve can be a bend. In one embodiment, the tissue engaging section 94 may optionally comprise a flexible memory-metal alloy, such as a nickel titanium allow for example, that has a preformed bend 97. As a result, when the tissue section 94 is constrained by the needle sheath 80 (as when the needle 54 is in a first retracted position) the tissue engaging section 94 is in a first configuration along a substantially longitudinal axis. When the needle 54 is in a second extended position such as when the needle is extended from the sheath distal opening 88 (not shown), then tissue engaging section 94 returns to a preformed unconstrained configuration. It should be understood that returning to a preformed unconstrained configuration does not exclude the possibility that the vessel walls constrain the tissue engaging section 94. Thus, a preformed bent configuration that is unconstrained includes any angle along a continuum from a constrained configuration within the sheath to a fully unconstrained configuration. Even though the preformed bend 97 is shown approximately at 20 degrees in FIG. 7C, the preformed bend 97 may comprise any angle suitable for the medical procedure intended for the device.

In FIG. 7D, the tissue engaging section 94 and the intermediate section 95 are operatively coupled via an integral joint 89. In one embodiment of the integral joint 89, the needle is extruded or molded so that the tissue engaging section 94 and intermediate section 95 are made up of different material. By way of example and not by way of limitation, the integral joint 89 may be formed utilizing an extrusion technique. For example, an integral joint 89 may be formed by extruding the tissue engaging section 94 using a first material (of greater flexibility or treated to have greater flexibility than a second material) and then extruding the intermediate section 95 using a second material (of lesser flexibility or treated to have lesser flexibility than the first material).

For example, the integral joint may be formed by extruding the tissue engaging section 94 using a first material that comprises a memory-metal alloy and then changing the composition or using different suitable second material (e.g., polymer, natural, synthetic, plastic, rubber, or metal, or combination thereof) in the extruder to extrude the intermediate section 95 from a composition or materials having less flexible properties relative to the first material of the tissue engaging section 94. More particularly, the first material may comprise, by way of example only and not by way of limitation, a memory-metal alloy such as, for instance only, a nickel titanium alloy, copper-zinc-aluminum, iron-manganese-silicon, gold-cadmium, copper-aluminum, and/or copper-aluminum-nickel or other alloy, composite, or polymer that is made to or is treated to have flexibility similar to a memory-metal alloy such that it is flexible and can accommodate some bending and twisting while still returning to its linear shape. In one embodiment, the intermediate section 95 comprises a second material such as, by way of example and not by way of limitation, stainless steel or similar alloy, a composite, a polymer, and/or a surgical stainless steel. As a result, the tissue engaging section 94 and intermediate section 95 are thereby formed from materials of different flexibility such that the tissue engaging section 94 has greater flexibility than the intermediate section 95. Alternatively, the sections 94, 95 may be operatively coupled by being formed integrally by, for example, extruding like materials to form sections 94, 95 having similar cross sectional areas and then treating, laminating, manufacturing and/or shaping the sections 94, 95 to make the tissue engaging section 94 more flexible than the intermediate section 95.

FIG. 7D also shows an embodiment wherein the tissue engaging section 94 has a preformed bend 97, and the intermediate section 95 is substantially linear having a longitudinal axis and a substantially constant radius. Of course, the intermediate section 95 may be flexible. The tissue engaging section 94 optionally comprises a flexible memory-metal alloy constrained by the needle sheath 80 when the needle 54 is in a first retracted position, and when the needle 54 is in a second extended position as when the needle is extended from the sheath distal opening 88 (not shown), the tissue engaging section 94 returns to its preformed unconstrained curved configuration.

FIG. 7E shows yet another embodiment of the needle 54, wherein the tissue engaging section 94 and intermediate section 95 are machined to be operatively coupled in an axial direction, the tissue engaging section 94 having greater flexibility than the intermediate section 95. The sections may be machined from materials of different flexibility—or from like materials treated, laminated, manufactured, or shape to have different flexibility—and having the same or substantially similar cross sectional area. Here, machining includes but is not limited to milling, turning, grinding, or laser machining the tissue engaging section 94 and intermediate section 95. In one embodiment, the tissue engaging section 94 comprises a memory-metal alloy such as, by way of example only, a nickel titanium alloy.

FIG. 7E also shows an embodiment wherein the needle distal end 91 further comprises an ultrasound marker 98. This marker 98 can be a material, such as gold, or it may be a shape such as a dimple or indentation that will result in an echo that shows up on the ultrasound. Other embodiments of the invention, such as FIGS. 7A through 7D may also comprise an ultrasound marker 98.

Methods

The invention also comprises a method 100 of using an elongate flexible surgical needle device for delivering medication and/or performing a biliary aspiration, whereby the needle 54 comprises a tissue engaging section 94 and an intermediate section 95 such that the tissue engaging section 94 having greater flexibility than an intermediate section 95. An embodiment of a method according to the invention is shown in FIG. 6.

In step 101, a needle device (e.g., 10, 11, 51) as taught herein above is provided, whereby the device is configured to be connected to a syringe (where the term "syringe" includes any instrument, device, machine, or apparatus comprising a mechanical, electrical, electromechanical, pneumatic, hydraulic, or combination thereof for delivering medication and/or for providing a source of negative pressure) and having an elongated surgical needle 54 moveable between first and second positions 110, 120, respectively. The surgical needle includes a proximal end 90 and a flexible distal end 91 that comprises a tissue engaging section 94 and an intermediate section 95 operatively coupled in an axial direction. The tissue engaging section 94 has greater flexibility than the intermediate section 95. Optionally, the tissue engaging section 94 comprises a memory-metal alloy, such as but not limited to a copper-zinc-aluminum alloy, a iron-manganese-silicon alloy, a gold-cadmium alloy, a copper-aluminum alloy, a copper-aluminum-nickel alloy, and/or a nickel-titanium alloy. In one embodiment, the needle assembly 51 has a length sufficient to reach the biliary tree of a patient.

In step 102, a syringe 15 is prepared and connected to the needle device as taught hereinabove (whereby the term "prepared" and variants thereof includes any means for creating desired suction and or filling with medication). The syringe 15 may be connected to the needle device and then prepared according to step 102, or may be prepared and then connected to the needle device according to step 102. In one embodiment for aspiration, the syringe is prepared in the following manner: the plunger locks 35 are depressed and the plunger rod 29 is fully advanced distally into the syringe chamber 25; the stopcock is turned to the closed position; the plunger rod 29 is pulled proximally until it is locked into place at the desired suction, as for example approximately 10 cubic centimeters; and the syringe 15 is set aside until the aspiration biopsy is desired. In an embodiment for medication, the plunger locks 35 are depressed and the plunger rod 29 is fully advanced distally into the syringe chamber 25; the stopcock is turned to the open position; and the plunger rod 29 is pulled proximally for uptake of medication until the plunger rod 29 is locked into place.

In step 103, the needle assembly 51 and more particularly the needle distal end 91 and still more particularly the tissue engaging section 94 is introduced to the appropriate position (e.g., a surgical site at or near the biliary tree of a patient) to deliver medication and/or for aspiration biopsy. By way of background, a physician may first advance an ultrasound endoscope to the appropriate position for biopsy, and then identify the desired biopsy site based on previous findings from endoscopy, radiography, and/or CT scans. In one embodiment, the needle assembly 51 with the needle 54 retracted within the optional sheath and/or endoscope is introduced into an accessory channel of the ultrasound endoscope. In one embodiment of step 102, the distal restraint 68 is locked while the distal end of the needle 54 is introduced. For example, a thumbscrew ring 68 may be locked at the zero centimeter mark according to the markings 73 on the stationary member 52.

In step 104, the first and second positions 110, 120, respectively, are set. In one embodiment, this means that the actuator 50 is set to a desired length. In another embodiment, the first and second positions 110, 120, respectively, correspond to the distance that at least the proximal end 90 of the needle 54 will move axially. Optionally, this is the distance between an adjustable member 53 first and second positions 110, 120, respectively. Other embodiments the first and second positions 110, 120, respectively, as previously described are incorporated by reference. Alternatively, the distal restraint 68 is moved from a first position 110 to a second position 120, as for example the moving of the thumbscrew ring 68 by loosening the thumbscrew 71, sliding the ring 69 axially to the desired second position, and then tightening the thumbscrew 71.

In step 105, the tissue engaging end 94 of the distal end 91 of the needle 54 is advanced distally to the surgical site for delivery of medication and/or aspiration biopsy. In one embodiment, this step comprises displacing the needle 54 from the first position 110 to the second position 120. Alternatively, this step comprises displacing the adjustable member 53 from the first position 110 to the second position 120. The other embodiments of moving the needle distal end 91 from first to second positions as previously described are incorporated by reference.

In step 106, the syringe is actuated (whereby the term "actuated" and variants thereof includes aspiration being applied to the target cells or tissue for biopsy and/or medication being delivered to the surgical site). In one embodiment, this involves connecting the syringe 15 to the main body 11 according to any of the configurations previously described for joining the syringe to the main body 11, its actuator 50, or either of its members 52, 53, respectively. If an optional stylet 81 is used in the device, then that should be removed before the syringe 15 is connected to the main body 11, its actuator 50, or either of its members 52, 53. Once the syringe 15 is so connected, the syringe stopcock 41 is turned to the open position allowing the negative pressure of the syringe chamber 25 to aspirate the cells or tissue or the plunger rod 29 to be depressed to deliver medication. If so desired, the needle 54 may be moved proximally and distally within the biopsy site.

After completion of the cell or tissue extraction and/or medication, the needle 54 may be retracted proximally back into the needle sheath 80 by proximally displacing the adjustable member 53. Then, the distal restraint 68 may be repositioned to the zero centimeter markings by reversing the earlier description. In an embodiment for aspiration, a specimen of the aspirate (cells or tissue) contained in the syringe may be prepared for examination by disconnecting the syringe, then pushing in the plunger rod 29 to expel the aspirate.

If additional samples are intended, as a time saving measure the device may be left in place and a separately prepared syringe may be connected according to the steps described above.

The foregoing methods need not be performed sequentially. Steps may be eliminated or combined. For example, the syringe may be prepared and connected (step 102) after the device is advanced to the surgical site (step 105). As another example, the positions may be set (step 104) before the needle assembly is introduced to a surgical site (step 103).

It is intended that the foregoing detailed description and corresponding figures of the medical devices, kits, and methods be regarded as illustrative rather than limiting. Terms have been used to describe embodiments of the invention, rather than being used lexicographically, unless a special definition of the term is clearly stated. As a result, it is intended that those terms and variants thereof should be given their reasonable plain and ordinary meaning.

Additional unclaimed features are shown in the figures and discussed in the description. Those additional features are not required to practice the invention, which is defined by the scope of the appended claims. Also, claim elements that are combined and/or replaced with equivalent elements are within the scope of the invention. Moreover, adding unclaimed features known in the art or developed hereafter do not avoid the intended scope or spirit of the present invention as defined by the appended claims.

While particular elements, embodiments and applications of the present invention have been shown and described, it will be understood, of course, that the invention is not limited thereto since modifications may be made by those skilled in the art, particularly in light of the foregoing teachings. Except where claimed below, the description herein and drawings shall not delimit any aspect of the invention. Therefore, it is contemplated by the appended claims to cover modifications to claimed elements, including equivalents to any claimed elements, as coming within the spirit and scope of the invention.

What is claimed is:

1. A surgical needle, comprising:
    an elongate biliary needle having a length from about 100 centimeters to about 250 centimeters, the biliary needle comprising a proximal end and an intermediate section comprising traditional biliary biopsy needle material and having a distal end portion;
    a flexible tissue engaging section having a length from about 1 centimeter to about 8 centimeters and comprising a tubular proximal lengthwise region and a tubular distal lengthwise region, the tubular proximal lengthwise region being formed from a first material comprising treated super-elastic alloy and the distal lengthwise region being formed from a second material comprising untreated super-elastic alloy, the tubular proximal lengthwise region having a proximal end abutting a distal end of the distal end portion of the biliary needle intermediate section;
    a butt joint that operatively couples the proximal end of the tubular proximal lengthwise region of the tissue engaging section and the distal end of the distal end portion of the biliary needle intermediate section; and
    a crimp sleeve comprising at least one or more of a glue, adhesive, resin, and chemical bonding material attached to an outer surface of the tubular proximal lengthwise region and to an outer surface of the distal end portion of the biliary needle at the butt joint,
    wherein the first material of the tissue engaging section has greater flexibility than the traditional biliary biopsy needle material of the biliary needle intermediate section,
    wherein the first material of the tissue engaging section proximal lengthwise region has greater flexibility than the second material of the tissue engaging section distal lengthwise region, and wherein the needle is suitable for delivery of one of medication and aspiration biopsy.

2. The device of claim 1 wherein the first material comprises a super-elastic alloy.

3. The device of claim 2 wherein the alloy is selected from the group consisting of a copper-zinc-aluminum alloy, a iron-manganese-silicon alloy, a gold-cadmium alloy, a copper-aluminum alloy, a copper-aluminum-nickel alloy, and a nickel-titanium alloy.

4. The device of claim 1 wherein the tissue engaging section and the intermediate section have substantially similar cross-sectional areas.

5. The device of claim 1 wherein the needle comprises a length of between about 200 cm and 215 cm.

6. The device of claim 1 wherein the needle is a biliary biopsy needle configured for performing aspiration of tissue in a biliary tree of a patient.

7. The device of claim 1 wherein the tissue engaging section has a preformed bend capable of being constrained to a substantially linear configuration and capable of returning to the preformed bend when unconstrained.

8. The device of claim 1 further comprising an elongate sheath having an opening at a proximal end and an opening at or near a flexible distal end, the sheath openings defining a channel there between, wherein the elongate needle is slideably positioned between first and second positions within the sheath channel.

9. The device of claim 8 further comprising a stationary member and an adjustable member moveable relative to the stationary member, the stationary member having openings at proximal and distal ends defining a channel therebetween, the proximal ends of the sheath and needle being positioned proximal to the stationary member distal opening and within the stationary member channel, and the adjustable member configured to move the needle between the first and second positions.

10. The device of claim 9 wherein the adjustable member has an opening at or near a proximal end, and an opening at or near a distal end and a channel in fluid communication within the stationary member channel.

11. The device of claim 10 further comprising a stylet having a proximal end and a distal end, the stylet configured to be removably placed in the adjustable member proximal opening such that the stylet extends within the adjustable member and stationary member channels and distally within a needle channel such that the stylet proximal end is located at or near the adjustable member proximal opening and the stylet distal end is located at or near the needle distal end.

12. The device of claim 11 further comprising a syringe configured to be in communication with the adjustable member proximal opening.

13. The device of claim 1 wherein the tissue engaging section proximal lengthwise region comprises super-elastic material and the tissue engaging section distal lengthwise region comprises a polymer.

14. The device of claim 1 further comprising an integral joint that secures the tissue engaging section proximal lengthwise region and the intermediate section, the integral joint comprising tensile strength and flexural strength.

15. The device of claim 1 further comprising a machined tissue engaging section proximal lengthwise region.

16. The device of claim 1 wherein the tissue engaging section distal lengthwise region further comprises an ultrasound marker.

17. The device of claim 1 wherein the butt joint comprises a weld.

18. The device of claim 1 wherein the first material of the tubular proximal lengthwise region comprises a laser-cut super-elastic alloy.

19. The device of claim 18 wherein the crimp sleeve is at least one glue, adhesive, resin, and chemical bonding material such that seals a laser-cut super-elastic alloy of the tubular proximal lengthwise region.

20. The device of claim 1 wherein the tubular proximal lengthwise region and distal end portion of the biliary needle have inner and outer diameters that are the same at the butt joint.

* * * * *

UNITED STATES PATENT AND TRADEMARK OFFICE
CERTIFICATE OF CORRECTION

PATENT NO.        : 7,641,638 B2                                                Page 1 of 1
APPLICATION NO. : 11/304218
DATED             : January 5, 2010
INVENTOR(S)       : Waxman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Sixteenth Day of November, 2010

David J. Kappos
*Director of the United States Patent and Trademark Office*